US011002730B2

(12) United States Patent
Kumar et al.

(10) Patent No.: US 11,002,730 B2
(45) Date of Patent: May 11, 2021

(54) MOLECULAR DESIGN TO SUPPRESS DESORPTION OF SELF-ASSEMBLED MONOLAYERS

(71) Applicant: International Business Machines Corporation, Armonk, NY (US)

(72) Inventors: Bharat Kumar, Tarrytown, NY (US); Sufi Zafar, Briarcliff Manor, NY (US); Ali Afzali-Ardakani, Ossining, NY (US)

(73) Assignee: International Business Machines Corporation, Armonk, NY (US)

( * ) Notice: Subject to any disclaimer, the term of this patent is extended or adjusted under 35 U.S.C. 154(b) by 95 days.

(21) Appl. No.: 15/986,960

(22) Filed: May 23, 2018

(65) Prior Publication Data

US 2019/0361011 A1 Nov. 28, 2019

(51) Int. Cl.
| | |
|---|---|
| *B01J 20/286* | (2006.01) |
| *G01N 33/53* | (2006.01) |
| *G01N 33/68* | (2006.01) |
| *G01N 33/82* | (2006.01) |
| *G01N 33/553* | (2006.01) |
| *G01N 33/543* | (2006.01) |
| *C12N 15/115* | (2010.01) |
| *G01N 33/566* | (2006.01) |

(52) U.S. Cl.
CPC ....... *G01N 33/5306* (2013.01); *C12N 15/115* (2013.01); *G01N 33/54346* (2013.01); *G01N 33/553* (2013.01); *G01N 33/566* (2013.01); *G01N 33/68* (2013.01); *G01N 33/82* (2013.01); *G01N 2610/00* (2013.01); *G01N 2650/00* (2013.01)

(58) Field of Classification Search
CPC ... B01J 20/286; G01N 33/5306; G01N 33/68; G01N 33/82; G01N 33/553; G01N 33/54346; G01N 33/566; G01N 2650/00; G01N 2610/00; G01N 33/54353; C12N 15/115

See application file for complete search history.

(56) References Cited

U.S. PATENT DOCUMENTS

| | | | |
|---|---|---|---|
| 7,078,192 B2 | 7/2006 | Linder et al. | |
| 8,062,491 B1 | 11/2011 | Gau | |
| 8,101,061 B2 | 1/2012 | Suh et al. | |
| 8,568,966 B2 | 10/2013 | Arinaga et al. | |
| 8,722,323 B2 | 5/2014 | Wohlstadter et al. | |
| 9,273,004 B2 * | 3/2016 | Afzali-Ardakani | ........................ C07D 213/76 |
| 2003/0113940 A1 * | 6/2003 | Erlanger | ............ A61K 51/0495 436/524 |
| 2004/0235050 A1 | 11/2004 | Linder et al. | |
| 2006/0223053 A1 | 10/2006 | Roper | |
| 2007/0003807 A1 * | 1/2007 | Wudl | ................. B01D 67/0044 423/447.2 |
| 2007/0170071 A1 | 7/2007 | Suh et al. | |
| 2008/0102213 A1 * | 5/2008 | Afzali-Ardakani | .... B82Y 30/00 427/378 |
| 2014/0162390 A1 * | 6/2014 | Afzali-Ardakani | ......................... G01N 33/5438 438/49 |
| 2014/0364325 A1 | 12/2014 | Cable et al. | |
| 2017/0066986 A1 | 3/2017 | Mezger et al. | |

OTHER PUBLICATIONS

Lou et al. ("Synthesis of Pyrene-Containing Polymers and Noncovalent Sidewall Functionalization of Multiwalled Carbon Nanotubes ", Chem. Mater., 2004, vol. 16, pp. 4005-4011). (Year: 2004).*
Lenfant et al. ("Electron Transport through Rectifying Self-Assembled Monolayer Diodes on Silicon: Fermi-Level Pinning at the Molecule-Metal Interface". J. Phys. Chem. B, 2006, vol. 110, pp. 13947-13958) (Year: 2006).*
Marek et al. ("Biotin-Pyrene Conjugates with Poly(ethylene glycol) Spacers Are Convenient Fluorescent Probes for Avidin and Streptavidin", Bioconjugate Chem. 1997, vol. 8, pp. 560-566) (Year: 1997).*
Cheng et al. ("Analytical Measurement of PEGylated Molecules", Bioconjugate Chem. 2012, vol. 23, pp. 881-899). (Year: 2012).*
Park, H.; Afzali, A.; Tulevski, G. S.; Franklin, A. D.; Tersoff, J.; Hannon, J. B.; Haensch W., High-density integration of carbon nanotubes via chemical self-assembly, Nature Nanotech. 2012, 7, 787-791.
Asenath, E.; Chen, S. W., How to Prevent the Loss of Surface Functionality Derived from Aminosilanes, Langmuir 2008, 24 (21), 12405-12409. [Abstract Only].
Kosian, M.; Smulders M. M. J.; Zuilhof, H., Structure and Long-Term Stability of Alkylphosphonic Acid Monolayers on SS316L Stainless Steel, Langmuir, 2016,32 (4), 1047-1057. [Abstract Only].
Bhairamadgi, N. S.; Pujari, S. P.; Trovela, S. G.; Debrassi, A.; Khamis, A. A.; Alonso, J. M.; Al Zahrani, A. A.; Wennekes, T.; Al Turaif, H. A.; van Rijn, C.; Alhamed, Y. A.; Zuilhof, H., Hydrolytic and Thermal Stability of Organic Monolayers on Various Inorganic Substrates, Langmuir 2014, 30 (20), 5829-5839 [Abstract Only].

* cited by examiner

*Primary Examiner* — Tracy Vivlemore
*Assistant Examiner* — Nam P Nguyen
(74) *Attorney, Agent, or Firm* — Patterson + Sheridan, LLP

(57) ABSTRACT

The compositions described herein include a substrate, wherein the substrate is a metal, metal oxide, metal nitride or a silicon containing material; a self-assembled monolayer (SAM) bonded to the substrate, wherein the self-assembled monolayer comprises: a surface binding unit bonded to the substrate, wherein the surface binding unit is selected from the group consisting of hydroxamates, phosphonates, catechols, halosilanes, alkoxysilanes, phosphonic acids, alkenes, alkynes, alcohols, 1,2-diols, and thiols; a separator unit bonded to the surface binding unit; a mass altering unit bonded to the separator unit; and a detector unit bonded to the separator unit.

13 Claims, 8 Drawing Sheets

MOLECULAR DESIGN TO SUPPRESS DESORPTION OF SELF-ASSEMBLED MONOLAYERS

BACKGROUND

The present disclosure relates to molecular detectors, and more specifically, the design of molecular detectors to suppress desorption of self-assembled monolayers from substrates.

Substrates can be functionalized with molecular detectors via self-assembly of monolayers. However, desorption of that self-assembled monolayer (SAM) from the substrate is an important limitation in detecting an analyte at low and ultra low concentrations. Since detection at such concentrations requires longer incubation times, the SAM can desorb from the substrate before the analyte attaches to the functionalized sensing surface of the substrate. Moreover, desorption of the SAM causes detection errors and signal drifts during analyte detection.

There is a need for suppressing desorption of molecular detectors from substrates.

SUMMARY

In an embodiment, a composition is provided. The composition includes a substrate, wherein the substrate is a metal, metal oxide, metal nitride or a silicon containing material; a self-assembled monolayer (SAM) bonded to the substrate, wherein the self-assembled monolayer comprises: a surface binding unit bonded to the substrate, wherein the surface binding unit is selected from the group consisting of hydroxamates, phosphonates, catechols, halosilanes, alkoxysilanes, phosphonic acids, alkenes, alkynes, alcohols, 1,2-diols, and thiols; a separator unit bonded to the surface binding unit; a mass altering unit bonded to the separator unit; and a detector unit bonded to the separator unit.

In another embodiment, a method is provided. The method includes modifying a substrate surface with a self-assembled monolayer (SAM), wherein the substrate is a metal, metal oxide, metal nitride, or a silicon containing material; adding a mass altering unit to the SAM by a chemical or physical reaction, wherein the SAM comprises: a surface binding unit bonded to the substrate, wherein the surface binding unit is selected from the group consisting of hydroxamates, phosphonates, catechols, halosilanes, alkoxysilanes, phosphonic acids, alkenes, alkynes, alcohols, 1,2-diols, and thiols; a separator unit bonded to the surface binding unit; and a detector unit bonded to the separator unit; and forming a molecular detector system.

In another embodiment, a method is provided. The method includes modifying a substrate surface with a self-assembled monolayer (SAM), wherein the substrate is a metal, metal oxide, metal nitride, or a silicon containing material; adding a mass altering unit to the SAM by a chemical or physical reaction, wherein the mass altering unit is a polymer, a fullerene, a nanotube, or a nanoparticle, and wherein the SAM comprises: a surface binding unit bonded to the substrate, wherein the surface binding unit is selected from the group consisting of hydroxamates, phosphonates, catechols, halosilanes, alkoxysilanes, phosphonic acids, alkenes, alkynes, alcohols, 1,2-diols, and thiols; a separator unit bonded to the surface binding unit; and a detector unit bonded to the separator unit; and forming a molecular detector system.

BRIEF DESCRIPTION OF THE SEVERAL VIEWS OF THE DRAWINGS

So that the manner in which the above recited features of the present disclosure can be understood in detail, a more particular description of the disclosure, briefly summarized above, may be had by reference to embodiments, some of which are illustrated in the appended drawings. It is to be noted, however, that the appended drawings illustrate only exemplary embodiments and are therefore not to be considered limiting of its scope, for the disclosure may admit to other equally effective embodiments.

DETAILED DESCRIPTION

Figure 1:
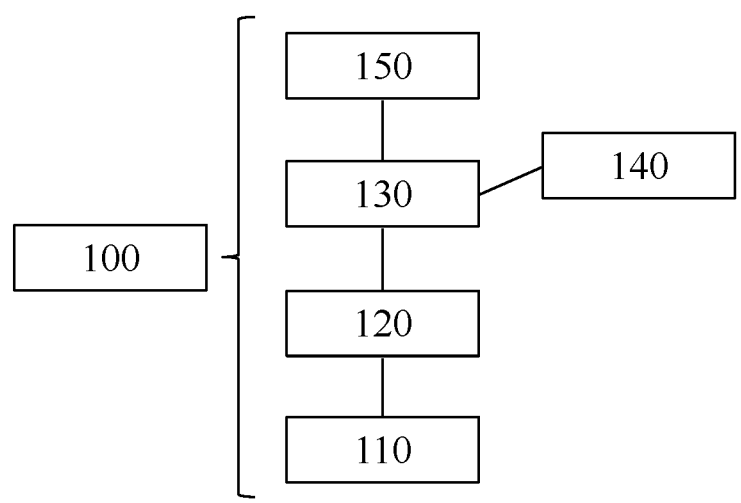
FIG. 1 is a representation of a molecular detection system according to some embodiments.

This disclosure relates to molecular detection systems, and to suppressing desorption of a self-assembled monolayer (SAM), having molecular detectors, from substrates. The desorption rate of the SAM from the substrate is inversely proportional to the mass of the SAM. Thus, according to the disclosure, a method of suppressing desorption of SAM from substrates includes increasing the mass of the SAM. Methods of suppressing desorption disclosed herein increase the mass of the SAM without significantly interfering with the target analyte binding to the functionalized surface. Thus, the molecular detection systems disclosed herein can be used to detect various target analytes.

This disclosure includes chemical structures that show atomic compositions of compounds and relative bonding arrangements of atoms in a chemical compound. Unless specifically stated, the geometric arrangement of atoms shown in the chemical structures is not intended to be an exact depiction of the geometric arrangement of every embodiment, and those skilled in the chemical arts will recognize that compounds may be similar to, or the same as, the illustrated compounds while having different molecular shapes or conformations. For example, the structures denoted herein may show bonds extending in one direction, while embodiments of the same compound may have the same bond extending in a different direction. Additionally, bond lengths and angles, Van der Waals interactions, isoelectronic structures, and the like may vary among instances of the same chemical compound. Additionally, unless otherwise noted, the disclosed structures cover all stereoisomers, conformers, rotamers, isomers, and enantiomers of the represented compounds.

Chemical structures are labeled using numbers, or numbers and letters, in parentheses. Unless otherwise noted, chemical reactions are performed at ambient conditions or under slight heating with no special atmosphere or head space, and may be performed using standard organic solvents to manage mix properties such as viscosity and flow index. Standard procedures for quenching the reaction, solvent removal, and purification are performed.

For purposes of this disclosure, and unless otherwise noted, a "polymer" has two or more of the same or different monomer ("mer") units. "Different" as used to refer to mer units indicates that the mer units differ from each other by at least one atom or are different isomerically.

For purposes of this disclosure, and unless otherwise noted, the term "substituted" refers to a hydrogen group that has been replaced with a carbon atom, a heteroatom, or a heteroatom-containing group. For example, a "substituted hydrocarbyl" is a radical made of carbon and hydrogen where at least one hydrogen is replaced by a carbon atom, a heteroatom, or heteroatom-containing group.

The term "carbon substituted" refers to a substituted species where a hydrogen group has been replaced with a carbon atom.

The term "heterosubstituted" refers to a substituted species where a hydrogen group has been replaced with a heteroatom or heteroatom-containing group.

The following abbreviation may be used herein: RT is room temperature (and is between about 15° C. and 25° C. unless otherwise indicated).

For purposes of this disclosure, and unless otherwise noted, "alkoxides" include an alkyl group that is a $C_1$ to $C_{40}$ hydrocarbyl. The alkyl group may be straight chain, branched, or cyclic. The alkyl group may be saturated or unsaturated. In some embodiments, the alkyl group may include at least one aromatic group.

For purposes of this disclosure, and unless otherwise noted, the terms "hydrocarbyl radical," "hydrocarbyl," "hydrocarbyl group," "alkyl radical," and "alkyl" are used interchangeably throughout this document. Likewise, the terms "group," "radical," and "substituent" are also used interchangeably in this document. For purposes of this disclosure, "hydrocarbyl radical" refers to $C_1$-$C_{100}$ radicals, that may be linear, branched, or cyclic, and when cyclic, aromatic or non-aromatic. Examples of such radicals include methyl, ethyl, n-propyl, isopropyl, n-butyl, isobutyl, sec-butyl, tert-butyl, pentyl, iso-amyl, hexyl, octyl cyclopropyl, cyclobutyl, cyclopentyl, cyclohexyl, cyclooctyl, and their substituted analogues. Substituted hydrocarbyl radicals are radicals in which at least one hydrogen atom of the hydrocarbyl radical has been substituted, for example with at least one halogen (such as Br, Cl, F or I) or at least one functional group such as $C(O)R^*$, $C(O)NR^*_2$, $C(O)OR^*$, $NR^*_2$, $OR^*$, $SeR^*$, $TeR^*$, $PR^*_2$, $AsR^*_2$, $SbR^*_2$, $SR^*$, $BR^*_2$, $SiR^*_3$, $GeR^*_3$, $SnR^*_3$, and $PbR^*_3$ (where $R^*$ is independently a hydrogen or hydrocarbyl radical, and two or more $R^*$ may join together to form a substituted or unsubstituted saturated, partially unsaturated or aromatic cyclic or polycyclic ring structure), or, for example, where at least one heteroatom has been inserted within a hydrocarbyl ring.

For purposes of this disclosure, and unless otherwise noted, the term "alkenyl" refers to a straight-chain, branched-chain, or cyclic hydrocarbon radical having one or more double bonds. These alkenyl radicals may be optionally substituted. Examples of suitable alkenyl radicals include ethenyl, propenyl, allyl, 1,4-butadienyl cyclopropenyl, cyclobutenyl, cyclopentenyl, cyclohexenyl, cycloctenyl, including their substituted analogues.

For purposes of this disclosure, and unless otherwise noted, the term "alkoxy" or "alkoxide" refers to an alkyl ether or aryl ether radical wherein the term alkyl is as defined above. Examples of suitable alkyl ether radicals include methoxy, ethoxy, n-propoxy, iso-propoxy, n-butoxy, iso-butoxy, sec-butoxy, tert-butoxy, and phenoxyl.

For purposes of this disclosure, and unless otherwise noted, the term "aryl" or "aryl group" includes a $C_4$-$C_{20}$ aromatic ring, such as a six carbon aromatic ring, and the substituted variants thereof. Likewise heteroaryl refers to an aryl group where a ring carbon atom (or two or three ring carbon atoms) has been replaced with a heteroatom, preferably N, O, or S. As used herein, the term "aromatic" also refers to pseudoaromatic heterocycles which are heterocyclic substituents that have similar properties and structures (nearly planar) to aromatic heterocyclic ligands, but are not by definition aromatic; likewise the term aromatic also refers to substituted aromatics.

For purposes of this disclosure, and unless otherwise noted, where isomers of a named alkyl, alkenyl, alkoxide, or aryl group exist (e.g., n-butyl, iso-butyl, iso-butyl, or tert-butyl) reference to one member of the group (e.g., n-butyl) shall expressly disclose the remaining isomers (e.g., n-butyl, iso-butyl, sec-butyl, and tert-butyl) in the family. Likewise, reference to an alkyl, alkenyl, alkoxide, or aryl group without specifying a particular isomer (e.g., butyl) expressly discloses all isomers (e.g., n-butyl, iso-butyl, sec-butyl, and tert-butyl).

For any particular compound disclosed herein, any general or specific structure presented also encompasses all conformational isomers, regioisomers, and stereoisomers that may arise from a particular set of substituents, unless stated otherwise. Similarly, unless stated otherwise, the general or specific structure also encompasses all enantiomers, diastereomers, and other optical isomers whether in enantiomeric or racemic forms, as well as mixtures of stereoisomers, as would be recognized by a skilled artisan.

For purposes of this disclosure, and unless otherwise noted, "ring structure" refers to atoms bonded together in one or more cyclic arrangements.

For purposes of this disclosure, and unless otherwise noted, the term "ring atom" refers to an atom that is part of a cyclic ring structure. By this definition, a benzyl group has six ring atoms and tetrahydrofuran has 5 ring atoms.

For purposes of this disclosure, and unless otherwise noted, a heterocyclic ring is a ring having a heteroatom in the ring structure as opposed to a ring where a hydrogen on a ring atom is replaced with a heteroatom. For example, tetrahydrofuran is a heterocyclic ring and 4-N,N-dimethyl-amino-phenyl is a heteroatom-substituted ring.

For purposes of this disclosure, and unless otherwise noted, the term "aromatic" also refers to pseudoaromatic heterocycles which are heterocyclic substituents that have similar properties and structures (nearly planar) to aromatic heterocyclic ligands, but are not by definition aromatic; likewise, the term aromatic also refers to substituted aromatics.

FIG. 1 shows a design of a molecular detector system 100 (also referred to as a molecular detection system) according to some embodiments. The molecular detector system 100 includes a substrate 110 and a surface binding unit 120 that can bind (chemically and/or physically) to the substrate 110. The molecular detector system 100 further includes a separator unit 130, which is bonded to the surface binding unit 120, a mass-altering unit 140, and a detector unit 150. The mass altering unit 140 is bonded to the separator unit 130 and is used to add mass to the molecular detector system 100 in order to suppress desorption from the substrate 110. The molecular detector system 100 further includes a detector unit 150, which is also referred to as a molecular acceptor unit and/or a detection unit. The detector unit 150 is bonded to the separator unit 130 and is used to detect a target analyte through chemical or physical bonding.

In some embodiments, a mixture of molecular detector systems 100 can be formed. The mixture allows for detection of different molecules from a single analyte solution.

Substrate 110

The substrate 110 for the molecular detector system 100 includes any substrate that can be modified using self-assembled layers, such as metals, metal oxides, metal nitrides, and silicon-containing materials such as materials that are semiconductive and dielectric surfaces. Examples of metals include those metals in Group 6 (such as tungsten), Group 11 (such as silver and gold), and Group 12 (such as zinc). Heavily doped silicon can also be used as a substrate 110. Examples of metal oxides and metal nitrides include any oxide or nitride having a surface with an isoelectric point of 7 or higher. Examples of such oxides and nitrides include Group 4 oxides (such as hafnium oxide and titanium oxide), Group 6 nitrides (such as tungsten nitride), Group 12 oxides (such as zinc oxide), and Group 13 oxides (such as aluminum oxide). Examples of dielectric layers include silicon oxide on top of heavily doped silicon and silicon nitride on top of heavily doped silicon. Other substrates include glass, plastic, and parylene. In some embodiments, the glass, plastic, and parylene has a metal and/or metal oxide layers on its surface. In some embodiments, the substrate is cleaned by an $O_2$ plasma treatment or a thermal annealing.

Surface Binding Unit 120

The molecular detector system includes a surface binding unit 120. The surface binding unit 120 attaches to the substrate 110 of the molecular detector system 100. Surface binding units 120 include any unit that can bind to a particular substrate. Surface binding units 120 for metal oxide substrates include hydroxamates, phosphonates, and alcohols (such as catechols). Surface binding units 120 for silicon oxide substrates include halosilanes such as trichlorosilanes, alkoxysilanes such as trialkoxysilanes, phosphonic acids, alcohols, and 1,2-diols. Surface binding units 120 for silicon-containing substrates include alkenes, alkynes, and alcohols. Surface binding units 120 for metal substrates include thiols.

Figure 2:
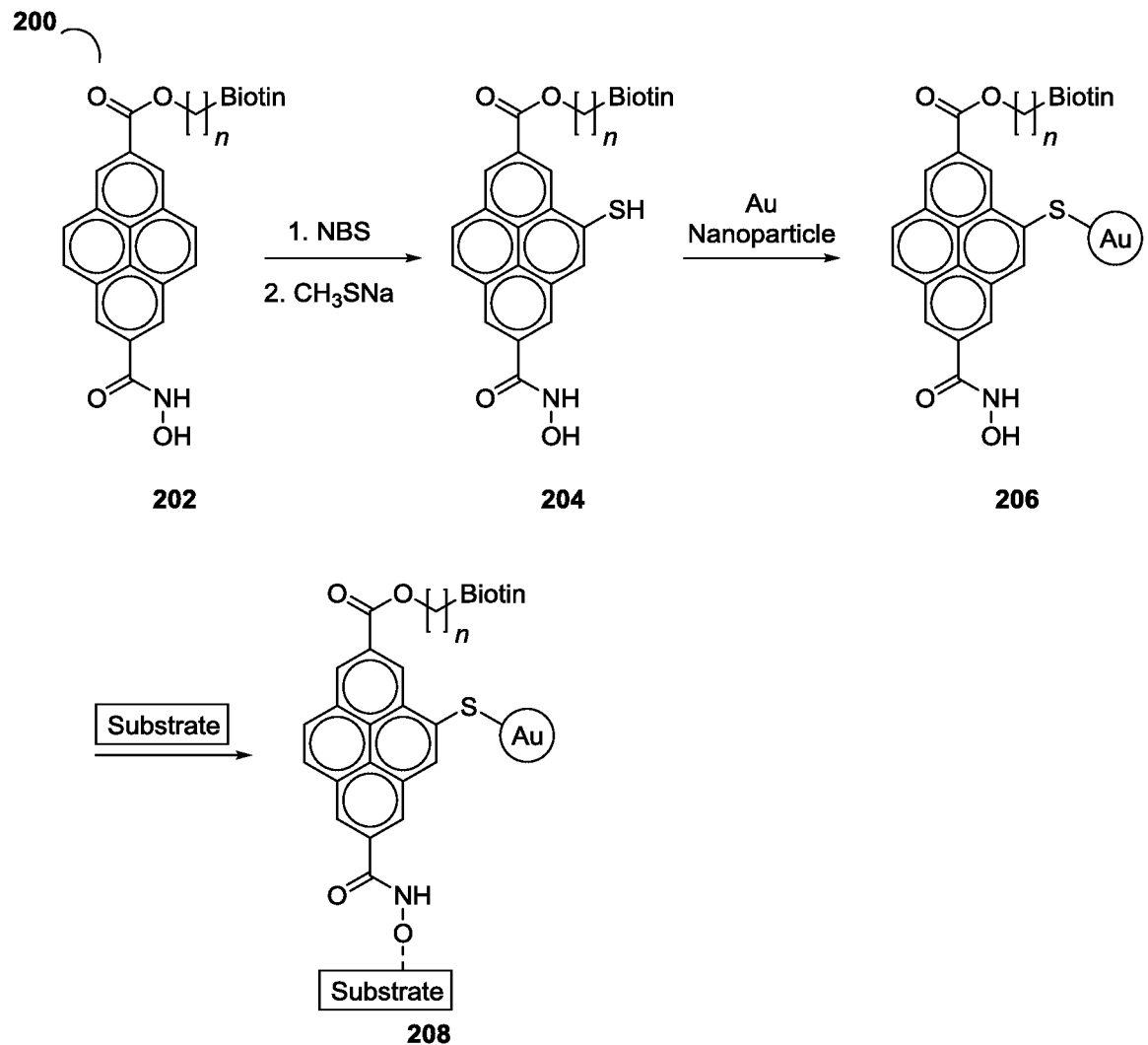
FIG. 2 is a chemical reaction diagram of a method 200 of forming a molecular detection system according to some embodiments.
Figure 3:
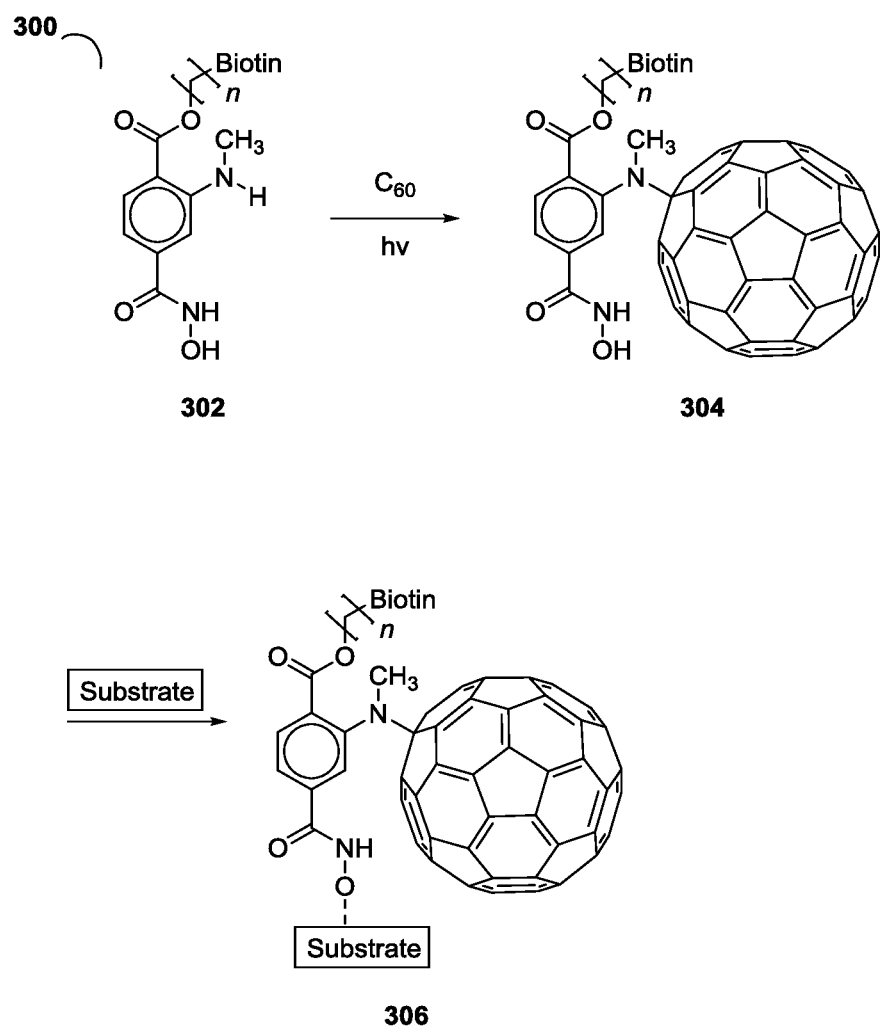
FIG. 3 is a chemical reaction diagram of a method 300 of forming a molecular detection system according to some embodiments.
Figure 4:
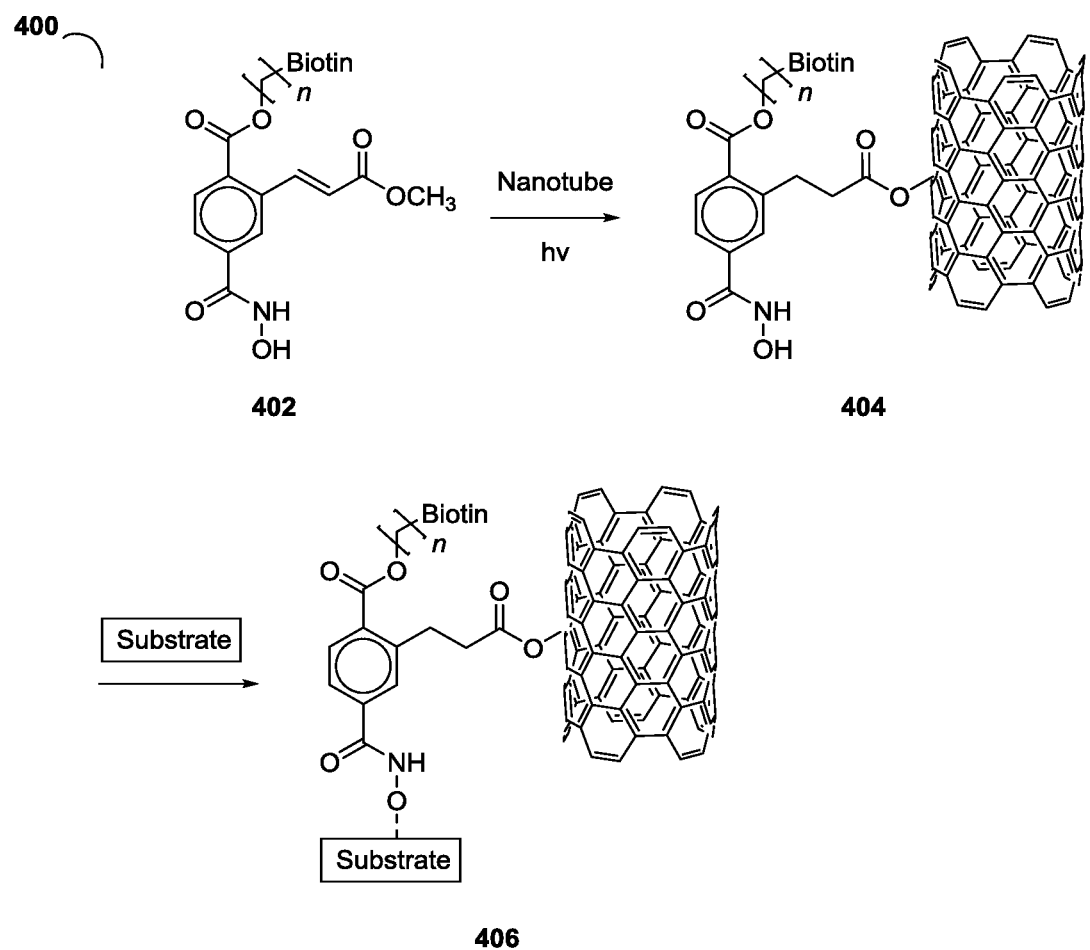
FIG. 4 is a chemical reaction diagram of a method 400 of forming a molecular detection system according to some embodiments.
Figure 5:
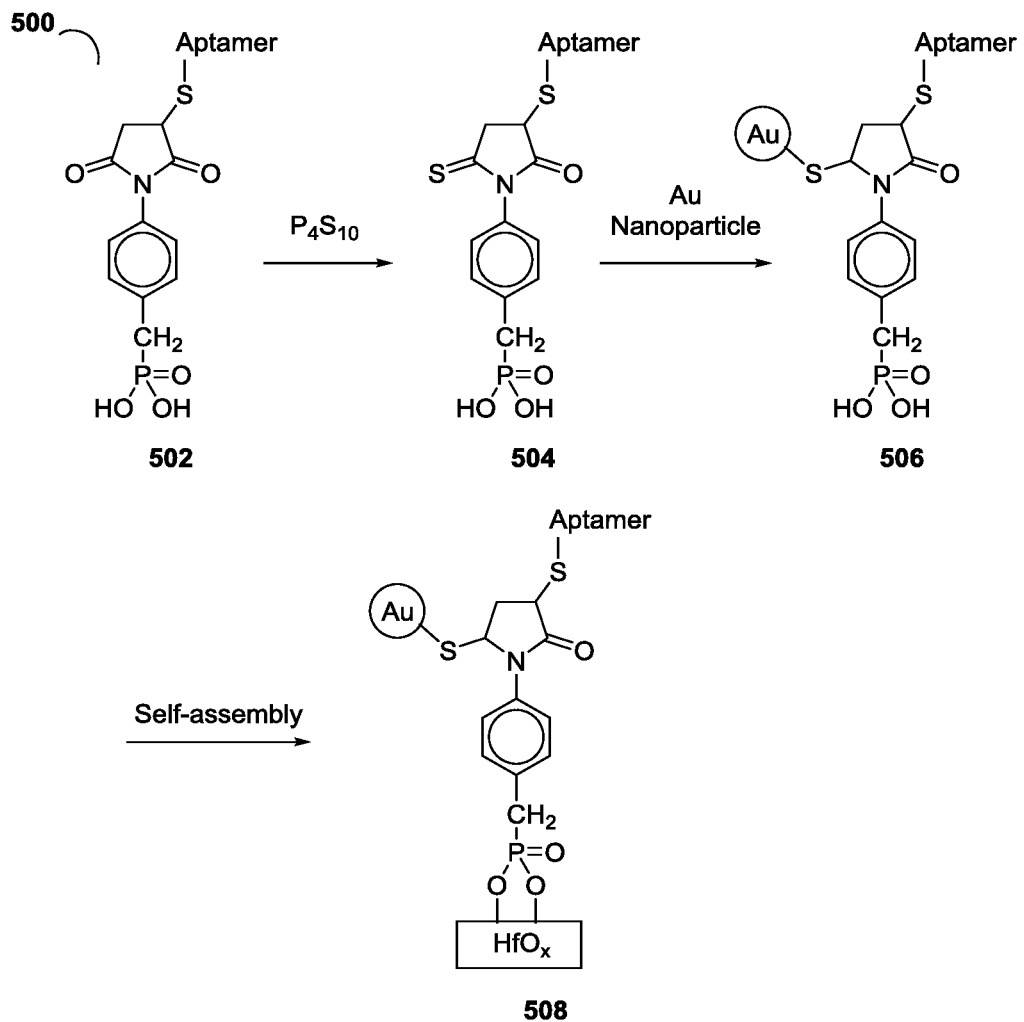
FIG. 5 is a chemical reaction diagram of a method 500 of forming a molecular detection system according to some embodiments.

FIGS. 2-4 show a hydroxamate surface binding unit (substrate not shown), and FIG. 5 shows a phosphonate as the surface binding unit.

Separator Unit 130

The molecular detector system 100 includes a separator unit 130. The separator unit 130 is attached to the surface binding unit 120, and provides a bonding site for the mass adjustment unit 140 and a bonding site for the detection unit 150. The separator unit 130 can be any separator unit that can bond to the surface binding unit 120, the detection unit 140, and the mass-altering unit 150.

Examples of the separator unit 130 include $C_1$ to $C_{40}$ hydrocarbyls (such as $C_1$ to $C_{16}$ unsubstituted and substituted alkyl radicals, $C_1$ to $C_{16}$ unsubstituted and substituted alkenyl radicals, and $C_1$ to $C_{16}$ unsubstituted and substituted alkynyl radicals), unsubstituted and substituted cyclic and polycyclic ring structures such as unsubstituted and substituted $C_4$ to $C_{62}$ ring structures, such as $C_4$ to $C_{30}$ cyclic and polycyclic ring structures (for example unsubstituted and substituted phenyl radicals, unsubstituted and substituted naphthyl radicals, unsubstituted and substituted anthracenyl radicals, unsubstituted and substituted phenanthrenyl radicals, unsubstituted and substituted pyrenyl radicals, and other aryl radicals). Unsubstituted and substituted heteroaryl radicals and unsubstituted and substituted heterocyclic radicals are also contemplated. Moreover, the cyclic and polycyclic ring structures do not have to be fully conjugated.

Mass Altering Unit 140

The molecular detector system 100 further includes a mass altering unit 140. The mass altering unit 140 can be any unit that can bind to the separator unit 130 and that adds mass. Examples of the mass altering unit 140 include polymers, carbon cages such as fullerenes, nanotubes, and nanoparticles such as gold nanoparticles.

Fullerenes can include any fullerene such as $C_{60}$ fullerenes, $C_{70}$ fullerenes, $C_{76}$ fullerenes, $C_{84}$ fullerenes, and $C_{100}$ fullerenes. A $C_{60}$ fullerene is shown in FIG. 3. Nanotubes can include any nanotube such as a (5,5)-armchair, a (6,6)-armchair, a (7,7)-armchair, a (8,8)-armchair, a (9,9)-armchair, a (10,10)-armchair, a (9,0)-zigzag, a (10,0)-zigzag, a (11,0)-zigzag, a (12,0)-zigzag, a (13,0)-zigzag, a (14,0)-zigzag, a (15,0)-zigzag, a (16,0)-zigzag, a (17,0)-zigzag, and a (18,0)-zigzag. A (5,5)-armchair nanotube is shown in FIG. 4. Any polymer that has a residual reactive group (e.g., olefin, halogen, amine, and carbonyl), either at a terminus or pendant from the polymer backbone, can act as the mass altering unit 140. The residual reactive group allows the polymer to bond with the separator unit 130. Such polymers include polyolefins such as polyethylene and polypropylene; polyvinyl chloride; polyethylene glycol; polyvinylacetate; polyurethane; polystyrene; nylon; nylon 6; nylon 6,6; and polytetrafluoroethylene, among others that will occur to skilled artisans. Nanoparticles that act as mass altering units 140 include gold nanoparticles and silver nanoparticles. Any of the mass-altering units can be substituted or unsubstituted.

Various functional groups can be used to attach the mass altering unit 140 to the separator unit 130, such as thiols, isothiocyantes, alkenes, alkynes, and amines. FIGS. 2 and 5 show a thiol group used to attach gold nanoparticles to the separator unit. Thiols can also be used to attach polymers to the separator unit. Isothiocyanates can be used to attach polymers to the separator unit 130 through, for example, click chemistry. Alkenes, alkynes, and esters can be used to attach polymers, fullerenes, and nanotubes to the separator unit as shown in FIG. 4. FIG. 3 shows an amine used to attach a fullerene to the separator unit.

Detector Unit 150

The molecular detector system 100 further includes a detector unit 150. The detector unit 150 can be any unit that can bind to the separator unit 130 and detect a target analyte. Examples of the detector unit 150 include biotin and aptamers (such as peptide aptamers, DNA aptamers, and RNA aptamers) that detect biomolecules. Aptamers can be used to detect small molecules, toxins, peptides, proteins, viruses, bacteria, and even whole cells. Other examples of the detector unit 150 include antibodies and crown ethers.

Various functional groups can be used to attach the detector unit 150 to the separator unit 130 such as esters, amides, phosphonates, and maleimides. For example, and as shown in FIG. 2, an ester functionality is used to attach biotin to the separator unit. Alternatively, an amide functionality can be used to attach biotin to the separator unit. As shown in FIG. 5, a maleimide-type functionality is used to attach aptamers to the separator unit through a sulfur group.

FIG. 2-5 show examples of molecular detector systems. In FIGS. 2-4, n is an integer from 1 to about 20. FIG. 2 illustrates an example of a molecular detector system 208 where the surface binding unit 130 (FIG. 1) is a hydroxamate, the separator unit 130 (FIG. 1) is a pyrenyl, the mass altering unit 140 (FIG. 1) is a gold nanoparticle connected through a thiol to the separator unit 130 (FIG. 1), and the detector unit 150 (FIG. 1) is biotin connected through an ester to the separator unit 130 (FIG. 1).

FIG. 2 also shows a method 200 of making the molecular detector 208 system according to some embodiments. Hydroxamate 202 may be prepared according to known procedures. According to some embodiments, hydroxamates 204 and 206 may be prepared according to the following procedure. Hydroxamate 202 (1 mmol) in anhydrous dimethylformamide (DMF, 10 ml) is treated with N-bromosuccinimide (NBS, 1.1 mmol) at about room temperature for about 8 hours. The mixture is added to 100 ml of water and extracted at least one time with diethylether. The combined ether extracts are washed with brine, dried over anhydrous magnesium sulfate, and the solvent evaporated to give the brominated product. Standard procedures for quenching, solvent removal, and purification are then performed to produce the brominated product (not shown). A solution of the brominated product in anhydrous DMF is made, and to this solution is added sodium thiomethoxide ($CH_3SNa$, 3 mmol), and heated under nitrogen at 100° C. for about 4 hours. The mixture is added to 100 ml of 1N dilute HCl. Standard procedures for quenching, solvent removal, and purification are then performed to produce hydroxamate 204. To a solution of hydroxamate 204 in a solvent such as DMF is added gold (Au) nanoparticles at room temperature. The solution is stirred at room temperature for about 24 hours, centrifuged, and the sediment was collected to give hydroxamate 206.

In some embodiments, the hydroxamate 206 is added to a substrate by the following procedure. A 5 mM solution of the hydroxamate (or phosphonic acid, or other unit that will form the monolayers on the substrate) was made in organic solvent (e.g., an alcohol solvent such as methanol, ethanol, and isopropanol). The substrate was pre-cleaned (by using $O_2$ plasma cleaning or by thermal annealing at about 300° C. or greater) and immersed in the solution of binding monomer for about 1 hour followed by rinsing with solvent. Standard procedures for solvent removal and purification are then performed to give molecular detector system 208. This procedure, or a similar procedure, can be used to attach the molecules described herein to the substrate 110 (i.e., for self assembly of monolayers).

FIG. 3 illustrates an example of a molecular detector system 306 with a hydroxamate surface binding unit, a phenyl separator unit, a $C_{60}$ fullerene mass altering unit connected through an amine to the separator unit, and a biotin detector unit connected through an ester to the separator unit.

FIG. 3 also shows a method 300 of making molecular detector system 306 according to some embodiments. Hydroxamates 302 and 304 may be prepared according to the following procedure. Hydroxamate 302 is prepared starting from a corresponding nitro compound in the ortho position to the ester connecting the biotin which can be prepared according to known methods. According to known procedures, the nitro compound is reduced to an amine, treated with formaldehyde to form an imine, and the imine is reduced to N-methylamine. Conversion of hydroxamate 302 to hydroxamate 304 is performed by irradiating (hv) a solution of hydroxamate 302 and fullerene (e.g., $C_{60}$) in DMF under incandescent light for about 8 hours at about room temperature. Standard procedures for quenching, solvent removal, and purification are then performed to produce hydroxamate 304. Addition of the hydroxamate 304 to a substrate to form molecular detector system 306 is then performed by the self-assembly procedure described above. Standard procedures for solvent removal and purification are then performed to give molecular detector system 306.

FIG. 4 illustrates an example of a molecular detector system 304 with a hydroxamate surface binding unit, a phenyl separator unit, a nanotube (such as a (5,5) armchair carbon nanotube) mass altering unit connected through an ester to the separator unit, and a biotin detector unit connected through an ester to the separator unit.

FIG. 4 also shows a method 400 of making molecular detector system 406 according to some embodiments. Hydroxamates 402 and 404 may be prepared according to the following procedure. Hydroxamate 402 is prepared by a Heck reaction of the corresponding brominated ring with methyl acrylate according to known procedures. Standard procedures for quenching, solvent removal, and purification are then performed to produce hydroxamate 402. A dispersion of hydroxamate 402 and carbon nanotube in a solvent (e.g., DMF) is irradiated with ultraviolet (UV) light. Standard procedures for quenching, solvent removal, and purification are then performed to produce hydroxamate 404. Addition of the hydroxamate 404 to a substrate to form molecular detector system 406 may be performed by the self-assembly procedure described above. Standard procedures for solvent removal and purification are then performed to give molecular detector system 406.

FIG. 5 illustrates an example of a molecular detector system 508 with an aryl phosphonate surface binding unit, a maleimide-type separator unit, a gold nanoparticle mass altering unit connected through a sulfur atom to the separator unit, and an aptamer detector unit connected through a sulfur atom to the separator unit.

FIG. 5 also shows a method 500 of making a molecular detector system 508 according to some embodiments. Maleimide 502, thioketone 504, and thioether 506 may be prepared according to the following procedure. Maleimide 502 is prepared by reaction of 4-aminobenzyl phosphonic acid with maleimide, which in turn is reacted with a thiol terminated aptamer according to known procedures. Standard procedures for quenching, solvent removal, and purification are then performed to produce maleimide 502. Transformation of the ketone in maleimide 502 to the corresponding thioketone 504 may be performed according to known methods. For example, to a solution of maleimide 502 in a solvent (such as water) is added phosphorous decasulfide ($P_4S_{10}$) in the presence of aluminum oxide. Standard procedures for quenching, solvent removal, and purification are then performed to produce thioketone 504.

To a solution of thioketone 504 in a solvent such as water is added gold (Au) nanoparticles at room temperature. The solution is stirred at room temperature for about 24 hours and centrifuged, and the sediment is collected to give thioether 506. The substrate for the phosphonic acid can be a hafnium oxide ($HfO_x$) substrate as shown by molecular detector system 508. Addition of the thioether 506 to a substrate (e.g., $HfO_x$) to form molecular detector system 508 may be performed by the self-assembly procedure described above.

The examples in FIGS. 2-5 show that the surface binding unit (e.g., hydroxamate or phosphonate surface binding functionality) can be used with any of the separator units, mass altering units, and detector units described herein. For example, the gold nanoparticle can be replaced with silver or with a polymer, as described herein.

Figure 6A:
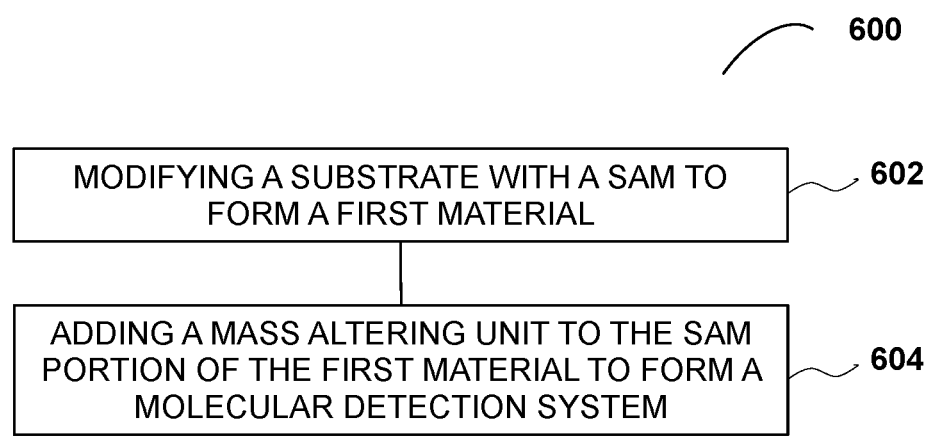
FIG. 6A is a block diagram illustrating a method 600 of making a molecular detection system according to some embodiments.

FIG. 6A is a block diagram illustrating a method 600 of making a molecular detection system according to some embodiments. The method 600 includes modifying a substrate with a SAM to form a first material at operation 602. In some embodiments, the SAM includes a detector unit. The substrate can be any substrate disclosed herein. The method 600 further includes adding a mass altering unit to the SAM portion of the first material to form a molecular detection system at operation 604. The mass altering unit can be any mass altering unit described herein.

Figure 6B:
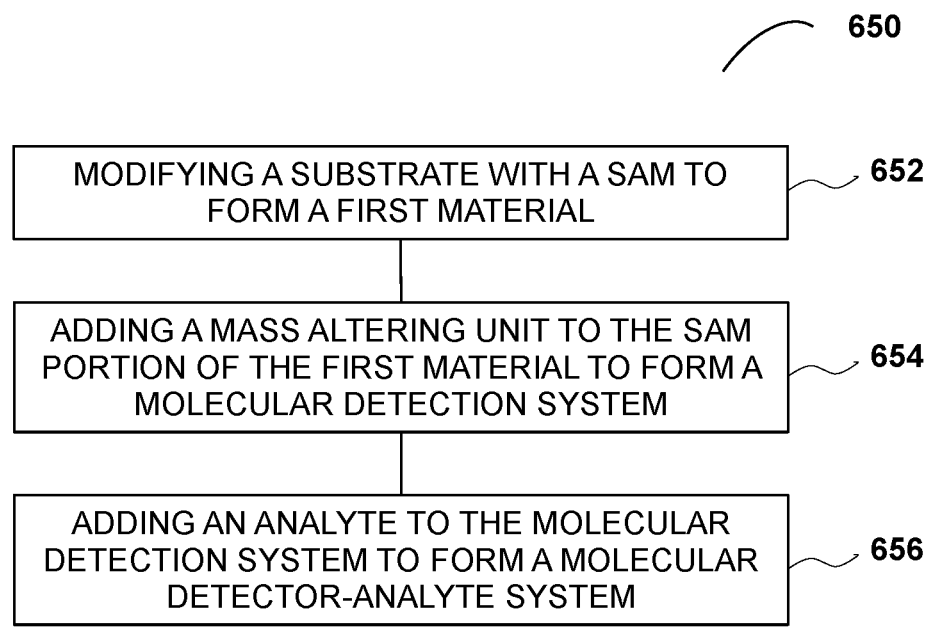
FIG. 6B is a block diagram illustrating a method 650 of making a molecular detection system according to some embodiments.

FIG. 6B is a block diagram illustrating a method 650 of making a molecular detection system according to some embodiments. Operations 652 and 654 correspond to operations 602 and 604 of FIG. 6A. The method 650 further includes adding an analyte (such as streptavidin) to the molecular detection system to form a molecular detector-analyte system at operation 656. The detector unit for this molecular detection system can include biotin. In some embodiments, the analyte can include small molecules, toxins, peptides, proteins, viruses, bacteria, whole cells, other biomolecules, or a combination thereof. The detector unit for this molecular detection system can include aptamers (such as peptide aptamers, DNA aptamers, and RNA aptamers).

Figure 7:
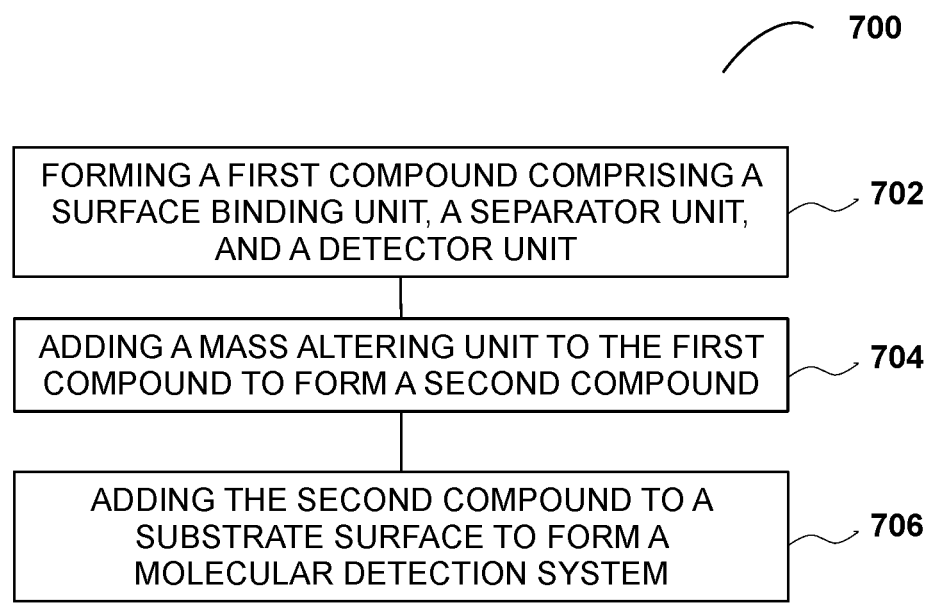
FIG. 7 is a block diagram illustrating a method 700 of making a molecular detection system according to some embodiments.

FIG. 7 is a block diagram illustrating a method 700 of making a molecular detection system according to some embodiments. The method 700 includes forming a first compound comprising a surface binding unit, a separator unit, and a detector unit at operation 702. The surface binding unit can be any surface binding unit disclosed herein; the separator unit can be any separator unit disclosed herein; and the detector unit can be any detector unit disclosed herein. The method 700 further includes adding a mass altering unit to the first compound to form a second compound at operation 704. The mass altering unit can be any mass altering unit described herein. The method 700 further includes adding the second compound to a substrate to form a molecular detection system at operation 706. The second compound forms a self-assembled monolayer (SAM) on the substrate. The substrate can be any substrate disclosed herein.

The descriptions of the various embodiments of the present disclosure have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

While the foregoing is directed to embodiments of the present disclosure, other and further embodiments of the disclosure may be devised without departing from the basic scope thereof, and the scope thereof is determined by the claims that follow.

What is claimed is:

1. A method comprising:
   modifying a substrate surface with a self-assembled monolayer (SAM), wherein the substrate is a metal, metal oxide, metal nitride, or a silicon containing material;
   adding a mass altering unit to the SAM by a chemical or physical reaction, wherein the mass altering unit consists of a polymer and wherein the SAM comprises:
      a surface binding unit bonded to the substrate, wherein the surface binding unit is selected from the group consisting of hydroxamates, phosphonates, catechols, halosilanes, alkoxysilanes, phosphonic acids, alkenes, alkynes, alcohols, 1,2-diols, and thiols;
      a separator unit bonded to the surface binding unit; and
      a detector unit bonded to the separator unit; and
   forming a molecular detector system.

2. The method of claim 1, wherein the separator unit is selected from the group consisting of a $C_1$ to $C_{40}$ hydrocarbyl, a $C_4$ to $C_{30}$ cyclic structure, a $C_4$ to $C_{30}$ polycyclic structure, and a $C_4$ to $C_{30}$ heterocyclic structure.

3. The method of claim 1, wherein the separator unit is selected from the group consisting of a $C_1$ to $C_{16}$ unsubstituted alkyl radical, a $C_1$ to $C_{16}$ substituted alkyl radical, a $C_1$ to $C_{16}$ unsubstituted alkenyl radical, a $C_1$ to $C_{16}$ substituted alkenyl radical, a $C_1$ to $C_{16}$ unsubstituted alkynyl radical, a $C_1$ to $C_{16}$ substituted alkynyl radical, an unsubstituted phenyl radical, a substituted phenyl radical, an unsubstituted naphthyl radical, a substituted naphthyl radical, an unsubstituted anthracenyl radical, a substituted anthracenyl radical, an unsubstituted phenanthrenyl radical, a substituted phenanthrenyl radical, an unsubstituted pyrenyl radical, and a substituted pyrenyl radical.

4. The method of claim 1, wherein the polymer is a polyethylene glycol, a polystyrene, polyvinylacetate, or a polyurethane.

5. The method of claim 1, wherein the detector unit is biotin, a peptide aptamer, a DNA aptamer, or a RNA aptamer.

6. The method of claim 1, wherein the detector unit is bonded to the separator unit through an ester.

7. The method of claim 6, wherein the separator unit is selected from the group consisting of a $C_1$ to $C_{40}$ hydrocarbyl, a $C_4$ to $C_{30}$ cyclic structure, a $C_4$ to $C_{30}$ polycyclic structure, and a $C_4$ to $C_{30}$ heterocyclic structure.

8. The method of claim 6, wherein the separator unit is selected from the group consisting of a $C_1$ to $C_{16}$ unsubstituted alkyl radical, a $C_1$ to $C_{16}$ substituted alkyl radical, a $C_1$ to $C_{16}$ unsubstituted alkenyl radical, a $C_1$ to $C_{16}$ substituted alkenyl radical, a $C_1$ to $C_{16}$ unsubstituted alkynyl radical, a $C_1$ to $C_{16}$ substituted alkynyl radical, an unsubstituted phenyl radical, a substituted phenyl radical, an unsubstituted naphthyl radical, a substituted naphthyl radical, an unsubstituted anthracenyl radical, a substituted anthracenyl radical, an unsubstituted phenanthrenyl radical, a substituted phenanthrenyl radical, an unsubstituted pyrenyl radical, and a substituted pyrenyl radical.

9. The method of claim 6, wherein the detector unit is biotin, a peptide aptamer, a DNA aptamer, or a RNA aptamer.

10. A method comprising:
    modifying a substrate surface with a self-assembled monolayer (SAM), wherein the substrate is a metal, metal oxide, metal nitride, or a silicon containing material;
    adding a mass altering unit to the SAM by a chemical or physical reaction, wherein the mass altering unit consists of a polymer, and wherein the SAM comprises:
       a surface binding unit bonded to the substrate, wherein the surface binding unit is selected from the group consisting of hydroxamates, phosphonates, catechols, halosilanes, alkoxysilanes, phosphonic acids, alkenes, alkynes, alcohols, 1,2-diols, and thiols;

a separator unit bonded to the surface binding unit, the separator unit selected from the group consisting of a $C_1$ to $C_{16}$ unsubstituted alkyl radical, a $C_1$ to $C_{16}$ substituted alkyl radical, a $C_1$ to $C_{16}$ unsubstituted alkenyl radical, a $C_1$ to $C_{16}$ substituted alkenyl radical, a $C_1$ to $C_{16}$ unsubstituted alkynyl radical, a $C_1$ to $C_{16}$ substituted alkynyl radical, an unsubstituted phenyl radical, a substituted phenyl radical, an unsubstituted naphthyl radical, a substituted naphthyl radical, an unsubstituted anthracenyl radical, a substituted anthracenyl radical, an unsubstituted phenanthrenyl radical, a substituted phenanthrenyl radical, an unsubstituted pyrenyl radical, and a substituted pyrenyl radical; and a detector unit bonded to the separator unit, wherein the detector unit is biotin, a peptide aptamer, a DNA aptamer, or a RNA aptamer; and forming a molecular detector system.

11. The method of claim 10, wherein the polymer is a polyethylene glycol, a polystyrene, polyvinylacetate, or a polyurethane.

12. The method of claim 10, further comprising adding an analyte to the molecular detection system.

13. The method of claim 10, wherein the detector unit is a peptide aptamer, a DNA aptamer, or a RNA aptamer.

* * * * *